United States Patent [19]

Serota et al.

[11] Patent Number: 4,477,384

[45] Date of Patent: Oct. 16, 1984

[54] PREPARATION OF α-SUBSTITUTED ACRYLIC ACIDS

[75] Inventors: Samuel Serota, Philadelphia; Warner M. Linfield, Oreland, both of Pa.

[73] Assignee: The United States of America as represented by the Secretary of Agriculture, Washington, D.C.

[21] Appl. No.: 236,084

[22] Filed: Feb. 20, 1981

[51] Int. Cl.³ .................. C07D 263/14; C08H 17/36; C07C 69/52; C07C 57/02
[52] U.S. Cl. ........................... 260/410.9 R; 260/413; 260/410.9 N; 260/410; 548/237; 548/239; 560/205; 562/598
[58] Field of Search ............... 548/237, 239; 560/205; 562/598; 260/410.15, 410.9 R, 410.9 N, 410, 413 R

[56] References Cited

U.S. PATENT DOCUMENTS

| | | | |
|---|---|---|---|
| 2,734,074 | 2/1956 | Redmon | 560/210 |
| 3,247,248 | 4/1966 | Sims et al. | 562/598 |
| 3,466,208 | 9/1969 | Wehrmeister | 562/598 |
| 3,493,635 | 2/1970 | Davies et al. | 548/237 |
| 3,687,922 | 8/1972 | Gisser et al. | 526/181 |
| 3,726,893 | 4/1973 | Chen et al. | 548/237 |
| 3,912,772 | 10/1975 | Pfeffer et al. | 562/598 |
| 3,953,432 | 4/1976 | Wehrmeister | 548/237 |
| 4,092,326 | 5/1978 | Shipchandler | 548/237 |

OTHER PUBLICATIONS

Journal of the American Chemical Society, vol. 89, No. 10, May 10, 1967, p. 2500, Creger, p. L., "Metalated Carboxylic Acids, I. Alkylation".
Journal of Organic Chemistry, vol. 37, No. 8, 1972, pp. 1256-1258, Pfeffer, Philipe, Kinsel, Edward and Silbert, Leonard S., "αAnions of Carboxylic acids V. A Simple High Presentation of α-Alkylhydracrylic Acids and α-Alkylacrylic Acids".
Mannich et al., Berichte, 65, 378, 1932.

Primary Examiner—Glennon H. Hollrah
Assistant Examiner—Raymond Covington
Attorney, Agent, or Firm—M. Howard Silverstein; William E. Scott; David G. McConnell

[57] ABSTRACT

α-Substituted acrylic acids are prepared from carboxylic acids in high yield and high purity by novel process. The α-substituted acrylic acids are prepared by condensing a fatty acid with 2-amino-2-methylpropanol, neutralizing the resulting oxazoline reaction mixture, converting the oxazoline with paraformaldehyde to an intermediate which is heated with an azetrope such as cumene or xylene and the resulting methylene oxazoline hydrolyzed to obtain the desired product.

7 Claims, No Drawings

PREPARATION OF α-SUBSTITUTED ACRYLIC ACIDS

BACKGROUND OF THE INVENTION

1. Field of the Invention

This invention relates to the preparation of α-alkyl and α-aryl substituted acrylic acids and esters and more particularly to those derived from fatty acids such as lauric, myristic, palmitic, stearic and oleic acid. The invention also relates to a process for making the substituted acrylic acids in high yield and high purity.

2. Description of the Prior Art

The preparation of α-substituted acrylic acids is known in the art. However, these known methods are not useful except for the preparation of laboratory scale quantities, because these methods require that the heat of reaction be controlled to avoid the production of numerous by-products. In one of the more recent methods, Pfeffer et al (U.S. Pat. No. 3,912,772 and J. Org. Chem. 37, 1256, 1972) modified Creger's synthesis (JACS 89, 2500, 1967) in tetrahydrofuran at low temperature by the use of hexamethylphosphoramide. It is known in the art, U.S. Pat. Nos. 2,734,074 and 3,247,248, that formaldehyde reacts with lower alkyl esters of aliphatic monocarboxylic acids having at least two hydrogen atoms attached to the α-carbon atom to produce lower alkyl esters of α-β-unsaturated acids. The procedures work only for the lower molecular weight α-substituted acrylic acids and do not work for the non-vaporizable higher molecular weight fatty acids of the subject invention. Gisser et al (U.S. Pat. No. 3,687,922) disclose the production of dodecylmalonic half acid-half ester which is reacted with diethylamine and formaldehyde to obtain methyl-α-n-dodecylacrylate. However, the yield is only 37% and the procedure requires the use of moisture sensitive and expensive reagents which are not needed in the instant invention.

SUMMARY OF THE INVENTION

An object of this invention is to provide a novel process for the preparation of α-alkyl and α-aryl substituted acrylic acids and esters.

Another object is to provide a process by which the α-substituted acrylic acids can be made in large quantities.

Still another object is to provide a process by which the α-substituted acrylic acids and esters can be prepared in high yield and high purity.

According to this invention the above objects are accomplished by a process wherein a carboxylic acid is condensed with 2-amino-2-methylpropanol (AMP) to obtain an oxazoline in a reaction mixture containing some unreacted acid, neutralizing the acid in the mixture with alkali, converting the oxazoline in the reaction mixture with paraformaldehyde to an intermediate mixture of mono- and bis- methylol derivatives of the oxazoline, heating the intermediate derivatives with an azeotrope such as cumene or xylene to obtain α-methylene oxazoline and hydrolyzing the methylene oxazoline.

DESCRIPTION OF THE INVENTION

The α-substituted acrylic acids are prepared in high yield and high purity by the process of this invention. They are useful in making polymers as additives to lubricants and hydraulic fluids, particularly as friction and wear reducing agents.

The compounds prepared by the process of this invention are represented by the formula

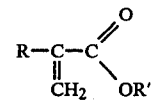

wherein R is an alkyl, aryl, aralkyl, alkenyl, cycloalkyl or alkylaryl radical having from 1 to 16 carbon atoms and R' is hydrogen or an alkyl, cycloalkyl, or alkenyl radical having from 1 to 3 carbon atoms.

The process can be run as a continuous operation in that the products formed as the process steps progress need not be isolated. Methods and tests that are well known in the art are used to follow the process to determine if it is proceeding as desired. A selected fatty acid is reacted as described later in the examples, with AMP to form a corresponding oxazoline. Since the reaction mixture containing the oxazoline contains some unreacted fatty acid, an alkali is added to neutralize the fatty acid and bring the pH of the reaction mixture to slightly above 7.0. We have found that this neutralization or pH control is very important to the success of our process. In the next step of the process, whereby the oxazoline in the reaction mixture is converted with paraformaldehyde to an intermediate mixture of mono- and bis-methylol derivatives of the oxazoline, the preceding control of pH with alkali diminishes formation of formic acid and other side reactions. The intermediate methylol derivatives are then heated with an azeotrope such as cumene or xylene to obtain methylene oxazoline which is hydrolyzed with a mixture of 3 to 4 N HCl, glacial acetic acid and water. Normalities below or above this range have been found to be inoperable in this process.

The following is a schematic representation of the process of the invention

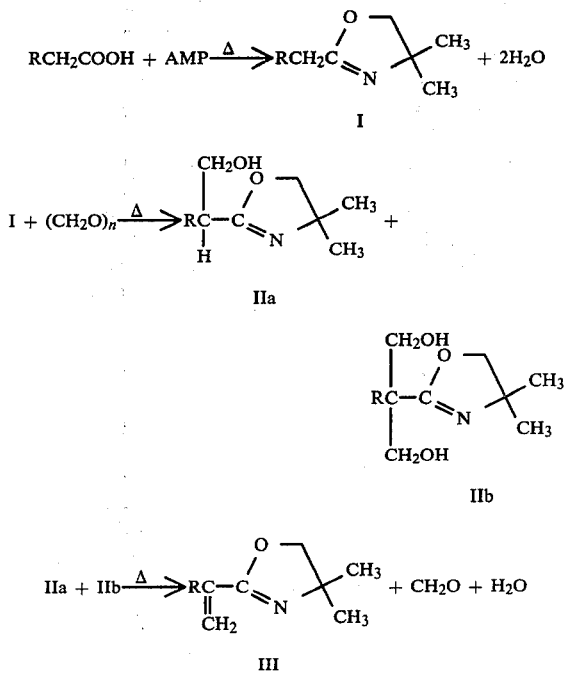

-continued

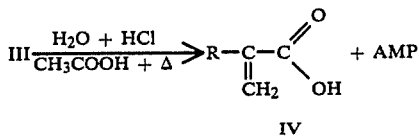

In the first step two moles of AMP are used for each mole of fatty acid so that the final fatty acid content will be about 2.0%. The excess AMP is recovered for recycling from the oxazoline product of the first step by distillation at or below atmospheric pressure and the free fatty acid is neutralized with a solution of alkali. This neutralization is very important to the process of this invention because without it as much as 30-40% of unwanted by-products are formed, thereby greatly reducing yield and purity of the desired product. The soap formed by the neutralization also suppresses formation of formate ester by-products in the ensuing process steps and also markedly reduces ester amide formation. In order to maximize yield and purity of desired product, the hydrolysis step should be repeated. In the case of the higher molecular weight α-acrylic acids, the crude product may be purified easily by treatment with a boron trifluoride-methanol complex.

The process of this invention may be carried out in any suitable apparatus made of any appropriate materials of construction such as stainless steel, alloy clad metals, ceramics and other similar materials, except for the hydrolysis step which requires HCl-resistant materials of construction.

The invention is exemplified by the following wherein Example 1 is the preferred method for making the higher molecular weight acids and Example 2 is the preferred method for making the lower molecular weight acids.

EXAMPLE 1

Synthesis of α-Tetradecylacrylic Acid

Palmitic acid (128.2 g, 0.5 moles) was stirred with AMP (89 g, 1 mole) in a 1 liter flask provided with stirrer, thermometer and a 12 inch Vigreux column. The reaction mixture was heated for 8.5 hours at such a rate that the vapor temperature on top of the column never exceeded 105° C. The reaction temperature gradually rose to 188° C. The free fatty acid content of the product after the heating period was 1.8%. 10% alcoholic potassium hydroxide solution (2 g) was added and heating as described above was continued for 3 hours. The excess AMP was removed by vacuum distillation at about 20 mm. The remaining free fatty acid was neutralized with additional 10% KOH solution. The crude oxazoline was heated to 90° C. and 24 g (0.8 moles) of paraformaldehyde was added. The temperature was maintained at 90° C. for 30 minutes and raised by 5° C. every half hour up to 115° C. Cumene (100 ml) was added and the mixture was refluxed for 2 ½ hours at 187° C. Gas liquid chromatography at 290° C. indicated that the product still contained 17% of unreacted oxazoline. The product was treated with an additional protion of paraformaldehyde (3.4 g), and the heating and reflux procedures as described above were repeated. The product contained 7% starting oxazoline. The product was freed from cumene by vacuum distillation at 20 mm at a maximum still temperature of 115° C. The oxazoline was then distilled at 142-152/0.05 min. Yield was 131 g (84.7% of theory). The residue weighed 21 g.

The distilled oxazoline was then hydrolyzed by refluxing overnight (16.5 hrs.) with a mixture of 100 ml concentrated HCl, 250 ml distilled water and 75 ml glacial acetic acid at 105° C. The layers were separated and the top layer was refluxed with a mixture of 50 ml of concentrated HCl, 100 ml distilled water and 30 ml of glacial acetic acid for a period of 6 hours. At this point, an IR spectrum showed no absorption at 1520 cm$^{-1}$ indicative of amide. The top layer was placed in a rotary evaporator and acetic acid and water were removed at 80° C. at 0.1 mm. The crude acid weighed 112 g (83.5% of theory). The product contained 96% fatty acid by titration with sodium hydroxide but contained about 14% unreacted palmitic acid by GLC analysis of the methylester.

Purification of α-Tetradecylacrylic Acid

Crude α-tetradecylacrylic acid, 110 g, containing 14% unreacted palmitic acid, m.p. 44°-47° C. was treated with 400 g methanol and 2.2 ml, boron trifluoride methanol complex (BF$_3$. 2 CH$_3$ OH) and the mixture allowed to stand for 1 hr. The solvent and BF were removed in a rotary evaporator and the residue recrystallized from 780 ml acetone at −10° C. Yield, 71 g containing 93% acid by titration and 95% of the desired acrylic acid. m.p. 49.5°-50° C. UV absorption at 206 nm confirmed the above analysis.

EXAMPLE 2

Synthesis of α-Pentylacrylic Acid

Heptanoic acid (65 g, 0.5 moles) was stirred with AMP (89 g, 1 mole) in a flask provided with stirrer, thermometer and a 12 inch Vigreux column. The reaction mixture was heated for 5 hours at such a rate that the vapor temperature on top of the condenser never exceeded 105° C. The reaction temperature gradually rose to 180° C. A sample withdrawn for free acid content was below 2%. A 10% alcoholic KOH solution (2 g) was added and refluxing was continued for 3 hrs. The excess AMP was removed by vacuum distillation through the Vigreux column until the vapor temperature reached 103° C/18 mm. The distillate was diluted with 100 ml of water and extracted with 25 ml of hexane. The hexane was evaporated and the residue was returned to the reaction vessel. Paraformaldehyde (24 g, 0.8 moles) was added to the reaction product, the crude oxazoline, at 90° C. The temperature was maintained at 90° C. for 30 minutes and raised by 5° C. every half hour up to 115° C. Cumene (100 ml) was added, and the mixture was refluxed for 3 hours at 180° C. Some cumene was removed to attain that temperature.

Gas-liquid chromatography at 170° C., indicated that the product contained 8.4% unreacted oxazoline. Paraformaldehyde (1.8 g, 0.06 moles) and 0.25 g of a 10% alcoholic KOH solution were added to the product which was heated stepwise from 90° C. to 115° C. as described above, and refluxed for 4 hours at 180° C. The product was then transferred to a 1 liter flask and refluxed overnight with 200 ml distilled water and 100 ml of concentrated HCl. The product was cooled to room temperature and the bottom layer was discarded. Hydrolysis was continued with 100 ml of distilled water and 50 ml concentrated hydrochloric acid for a period of 3 hours. The layers were separated as before, and the bottom layer discarded. The product was washed once with 50 ml of distilled water to remove residual hydrochloric acid. Phosphoric acid (85%, 2 g) was added to the product which was then distilled through a 12 inch Vigreux column under a water aspirator vacuum. The fraction boiling at 129° C. to 134° C. at 18 mm was collected. Towards the end of the distillation the product was heated to 300° C. to decompose any estolide. Yield of distillate was 45 g.

Purification of α-Pentylacrylic Acid

The distilled acid, 20 g, containing 14% of unreacted heptanoic acid, was treated at room temperature (22° C.) with 100 g absolute methanol and 0.4 ml of the methanol complex solution of boron trifluoride. After standing for 1 hr., 100 ml of water was added and the layers were separated. The water was extracted twice with 100 ml portions of hexane. The combined layer was freed from hexane by evaporation, and the residue was fractionally distilled. The forerun 2.7 g, boiling range 77°-120° C. vapor temperature at 20mm Hg contained mostly the methyl ester of the saturated acid. The residue, 15.4 g contained 98% acid by titration and consisted of 99% α-pentylacrylic acid according to the gas chromatographic analysis.

EXAMPLE 3

Preparation of α-Methylene Phenylacetic Acid

A mixture of 89 g (1 mole) of AMP and 68.1 g (0.5 moles) phenylacetic acid were heated together for 5 hours at such a rate that the vapor temperature on top of the attached vigreux column never exceeded 105° C. The temperature of the reaction mixture rose gradually to 176° C. At the end of the heating period the free fatty acid content was 0.6%. The excess AMP was removed by vacuum distillation (20mm) until the vapor temperature had risen to 105° C. The IR spectrum showed only a small content of ester.

To the crude oxazoline at 70° C. was added 2 g of 10% alcoholic potassium hydroxide, 0.3 g hydroquinone and 24 g (0.8 moles) of paraformaldehyde. The reaction was exothermic for 15 min. and the temperature rose to 80° C. The reaction mixture was then kept at 70° C. for 45 minutes. Xylene, 180 ml was added and the mixture refluxed through a Dean-Stark trap for 2.5 hrs. Gas chromatographic analysis showed the presence of 22% unreacted oxazoline. To the product was added 0.2 g hydroquinone, 0.1 g of 10% alcoholic potassium hydroxide and 4.5 g of paraformaldehyde at 70° C. The mixture was heated at 70° C. for 1 hr. and then refluxed for 30 min. Gas chromatography showed a 3.7% unreacted oxazoline content. Xylene was removed under vacuum and the product distilled at 87° C. to 95° C. at 0.2mm. Yield 69 g (69% of theory). Hydroquinone (0.3 g) was added to the freshly distilled oxazoline.

To 56 g of oxazoline were then added 50 ml concentrated hydrochloric acid, 100 ml distilled water and 35 ml of glacial acetic acid. The mixture was refluxed in a nitrogen atmosphere for 16 hours. To the cooled product, 150 ml of methylene chloride was added and after stirring for 5 minutes the bottom layer was separated. The organic layer was returned to the reaction flask and 25 ml of concentrated hydrochloric acid, 50 ml distilled water and 20 ml acetic acid were added. The methylene chloride was distilled off and the reaction mixture was refluxed for 3.5 hours. Methylene chloride (150 ml) was added and the layers separated as before. The product was dried in a rotary evaporator to remove methylene chloride and most of the acetic acid. The residue was dissolved in 150 ml methylene chloride. 100 ml distilled water was added and 25 g of 50% sodium hydroxide solution was added slowly with good agitation. The methylene chloride layer was then separated and evaporated to dryness. The residue weighed 12 g. Its IR spectrum showed a high ester content. The aqueous solution of the sodium salt of the desired acid was neutralized with about 25 ml of concentrated hydrochloric acid, and 150 ml of methylene chloride was added to dissolve the precipitated acid. The solvent was removed by evaporation and the residue dried in a vacuum oven. The crude acid contained 90% acid by titration, however, further purification was unsuccessful.

EXAMPLE 4

Synthesis of α-Benzylacrylic Acid

Hydrocinnamic acid, 75 g (0.5 mole) and AMP 89 g (1.0) was heated in a flask fitted with a Vigreux column for 6 hours as described above. The temperature rose to 188° C. and 20 ml of liquid distilled off. To the product, which was essentially free of acid, there was added 2 g of a 10% alcoholic KOH and heating was continued for 2 hours. The IR spectrum indicated absence of ester. AMP recovery for recycling was 40 g. To the crude oxazoline, paraformaldehyde, 24 g (0.8 mole) was added. After heating at 70° C. for one hour the reaction was 61.5% complete by GLC analysis at 230° C. The product was then heated at 80° C. for 90 min. and GLC analysis indicated 75.1% completion of reaction. After another hour at 90° C. the reaction was 89.2% complete. Xylene, 75 ml, was added and the mixture refluxed for 2 hours. The product contained 12.4% starting oxazoline by GLC analysis. Paraformaldehyde, 3 g, was added at 70° C. and the product heated at that temperature for one hour. Heating was continued at 80° C. for one hour and then at 90° C. for one hour. GLC analysis indicated 93.0% completion of the reaction. The product was refluxed for 2 hours and contained 96.7% of the desired oxazoline by GLC analysis.

Xylene was removed under vacuum and the crude oxazoline was refluxed overnight with 75 ml acetic acid, 100 ml concentrated HCl and 230 ml distilled water. The layers were separated and the water layer extracted with 100 ml dichloroethane and the residue added to the organic layer of the crude α-benzylacrylic acid. The latter was refluxed with 50 ml concentrated HCl, 125 ml distilled water and 37.5 ml acetic acid for three hours. The layers were separated, the aqueous layer extracted with 50 ml of dichloroethane and the extract and organic layer now combined. Solvent, water and acetic acid were removed by vacuum distillation. One gram of phosphoric acid, 85%, was added and the α-benzylacrylic acid distilled at 170°-174° C. at 20mm Hg. Yield 58.5 g (72% of theory), weight of residue 10.0 g. This product contained 97% acid by titration and 93.6% α-benzylacrylic acid by GLC analysis of its methyl ester. A portion of the product, which solidified upon standing, was recrystallized from hexane and melted at 66°-68° C. Its acid number corresponded to theory and it was 99% pure by GLC analysis of its methyl ester.

We claim:

1. A process for the preparation of α-substituted acrylic acids, comprising, condensing a carboxylic acid with 2-amino-2-methyl propanol, neutralizing the resultant oxazoline reaction mixture, reacting the oxazoline with paraformaldehyde, heating the resultant intermediate derivatives in the presence of an azeotrope to obtain the methylene oxazoline derivatives and hydrolyzing for about 16.5 hours the methylene oxazoline in the presence of a 3-4N mixture of HCl, glacial acetic and water.

2. A process for the preparation of α-alkyl and α-aryl substituted acrylic acids and esters of the formula

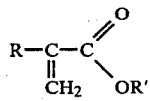

wherein R is selected from the group consisting of alkyl, aryl, aralkyl, alkenyl, cycloalkyl and alkylaryl radicals, having from 1 to 16 carbon atoms and R' is selected from the group consisting of hydrogen and alkyl, cycloalkyl and alkenyl radicals having from 1 to 3 carbon atoms, comprising the steps of (a) condensing a carboxylic acid with 2-amino-2-methyl-propanol;
(b) neutralizing with alkali the unreacted acid in the oxazoline reaction mixture obtained in step (a);
(c) reacting the oxazoline in the neutralized reaction mixture of steps (a) and (b) with paraformaldehyde;
(d) adding an azeotrope to the mono- and bis-methylol derivatives obtained in step (c) and heating the mixture;
(e) hydrolyzing the methylene oxazoline derivatives obtained in step (d) for about 16.5 hours in a 3-4N mixture of HCl, glacial acetic acid and water.

3. The process of claim 2 wherein the azeotrope is cumene.

4. The process of claim 2 wherein the azeotrope is xylene.

5. The process of claim 2 wherein the α-acrylic acid is further purified by treatment with a boron trifluoride-methanol complex.

6. In a process for the preparation of α-substituted acrylic acids wherein said acids are prepared by hydrolyzing an oxazoline, the steps which comprise
(a) condensing a carboxylic acid with 2-amino-2methyl-propanol to obtain a reaction mixture containing an oxazoline;
(b) neutralizing with alkali the unreacted acid in the oxazoline reaction mixture obtained in step (a);
(c) reacting the oxazoline in the neutralized reaction mixture of steps (a) and (b) with paraformaldehyde;
(d) adding an azeotrope to the mono-and bis-methylol derivatives obtained in step (c) and heating the mixture;
(e) hydrolyzing the methylene oxazoline obtained in step (d) for about 16.5 hours in a 3-4N mixture of HCl, glacial acetic acid and water; said reaction steps being conducted in a continuous manner thereby obviating the need to isolate the intermediate products from the reaction mixture.

7. In a method of preparing α-substituted acrylic acids wherein an oxazoline is prepared and isolated and the oxazoline hydrolyzed to obtain the desired acids, the improvement wherein unreacted acid in the oxazoline reaction mixture prepared from the condensation of a carboxylic acid with 2-amino-2-methylpropanol is neutralized with alkali and the pH adjusted to slightly above 7.0 prior to reacting the oxazoline with paraformaldehyde to convert it to a mixture of mono- and bis-methylol derivatives of oxazoline, heating said derivatives with an azeotrope to obtain α-methylene oxazoline and hydrolyzing the α-methylene oxazoline for about 16.5 hours in a 3-4N mixture of HCl, glacial acetic acid and water, said neutralization and subsequent reactions being conducted in situ.

* * * * *